(12) United States Patent
Drogue et al.

(10) Patent No.: US 7,717,890 B2
(45) Date of Patent: May 18, 2010

(54) FLUID AND BIOAEROSOL MANAGEMENT VACUUM CONNECTOR AND SYSTEM

(75) Inventors: Jeffrey K. Drogue, Minneapolis, MN (US); Leonard S. Schultz, Bloomington, MN (US); Barry M. Thompson, Maple Grove, MN (US)

(73) Assignee: Innovative Surgical Technologies, Inc., Eden Prairie, MN (US)

( * ) Notice: Subject to any disclaimer, the term of this patent is extended or adjusted under 35 U.S.C. 154(b) by 124 days.

(21) Appl. No.: 10/628,588

(22) Filed: Jul. 28, 2003
(Under 37 CFR 1.47)

(65) Prior Publication Data
US 2005/0251099 A1 Nov. 10, 2005

Related U.S. Application Data

(63) Continuation of application No. PCT/US02/02493, filed on Jan. 28, 2002.

(60) Provisional application No. 60/264,871, filed on Jan. 29, 2001.

(51) Int. Cl.
*A61M 1/00* (2006.01)
(52) U.S. Cl. .................. 604/315; 604/317; 604/319
(58) Field of Classification Search ............... 604/21, 604/35, 313–326; 95/268, 271, 273; 55/385.1, 55/418, 459.1, 467
See application file for complete search history.

(56) References Cited

U.S. PATENT DOCUMENTS

| 3,665,682 | A | * | 5/1972 | Ciavattoni et al. ............ 55/337 |
| 4,795,448 | A | | 1/1989 | Stacey et al. |
| 4,921,492 | A | | 5/1990 | Schultz et al. |
| 4,976,694 | A | * | 12/1990 | Schreibman ................. 604/140 |
| 5,019,060 | A | | 5/1991 | Goosen |
| 5,145,496 | A | * | 9/1992 | Mellen ......................... 55/337 |
| 5,195,995 | A | * | 3/1993 | Walker ....................... 604/319 |
| 5,242,434 | A | * | 9/1993 | Terry ........................... 604/317 |
| 5,264,026 | A | | 11/1993 | Paul |
| 5,578,000 | A | * | 11/1996 | Greff et al. ..................... 604/22 |
| 6,045,596 | A | * | 4/2000 | Holland et al. ............. 55/385.2 |
| 6,203,590 | B1 | * | 3/2001 | Byrd et al. ..................... 55/319 |

FOREIGN PATENT DOCUMENTS

WO    WO 89/05665    6/1989

* cited by examiner

*Primary Examiner*—Melanie J Hand
(74) *Attorney, Agent, or Firm*—David E. Bruhn; Dorsey & Whitney LLP

(57) ABSTRACT

The present invention comprises a central vacuum producing system suitable for collecting both liquid and gaseous material, one or more end effectors for use at a site at which liquid and gaseous material are produced, and a coupling device or connector for operably coupling one or more end effectors to the central vacuum. In this embodiment, the connector may be made of various materials, and may include a suitable liquid monitor or counter such as a flow meter.

11 Claims, 3 Drawing Sheets

FLUID AND BIOAEROSOL MANAGEMENT VACUUM CONNECTOR AND SYSTEM

CROSS-REFERENCE TO RELATED APPLICATION(S)

This application is a continuation of International Application No. PCT/US02/02493 filed on Jan. 28, 2002, and claims priority to said PCT application and to a U.S. Provisional application, Ser. No. 60/264,871, filed on Jan. 29, 2001. The international application was published under PCT Article 21(2) in English.

BACKGROUND OF THE INVENTION

The present invention relates to devices and methods for material handling and, in one embodiment, a fluid, i.e., gas and liquid, and bioaerosol management system and method suitable for use in the medical field. The present invention encompasses a method of handling, collecting, managing, measuring and/or disposing of fluids, including gases and liquids and, in some embodiments, solids.

The present invention may be well suited for use in the medical field, particularly in surgery, whether surgical procedures are being carried out in an operating room(s) or other clinical locations. It is well suited for use in controlling the flow of gases (e.g., air, inert gases, oxygen, etc.), liquids, fluids and bioaerosol and/or biohazardous material used or produced during surgical procedures. It provides for the removal of bioaerosols, fluids and liquids which are associated with surgical procedures, and provides for assessing or measuring the quantity of liquids, e.g., saline solution, blood, plasma, ascites and the like, produced or used during surgical procedures.

U.S. Pat. No. 5,019,060 (Goosen), U.S. Pat. No. 4,184,510 (Murry et al.), U.S. Pat. No. 4,704,106 (Shave et al.), U.S. Pat. No. 5,345,928 (Lindkvist) and U.S. Pat. No. 5,707,086 Treu et al.) disclose examples of the use of vacuum in the medical field, including a liquid collection device for use with surgical procedures (the U.S. Pat. No. 5,019,060). The disclosures of these five patents, particularly as to the use of vacuum in the medical field, are incorporated herein by reference.

U.S. Pat. No. 6,131,571 (Lampotang et al.), U.S. Pat. No. 5,836,909 (Cosmescu) and U.S. Pat. No. 4,453,937 (Kurtz et al.), disclose the use of various type of flow measuring devices including air flow meters (the U.S. Pat. No. 4,453,937), and/or pressure and/or flow and fluid sensors (the U.S. Pat. No. 5,836,909). The disclosures of these three patents, particularly as to the flow measuring and sensing devices, is incorporated herein by reference.

In one embodiment, the present invention comprises a system comprising a centralized evacuation system, one or more "end effectors" and a connector for operably coupling the one or more end effectors to the centralized evacuation system.

In one embodiment, the present invention comprises a connector for operably coupling one or more end effectors to a wall port of a central vacuum system, wherein the connector facilitates the coupling of the one or more end effectors and is adapted to receive both gaseous and liquid material. In some embodiments, the connector is adapted to separate gaseous and liquid material and, after the separation, collect and measure the quantity of liquid material, and, in some embodiments, to measure and/or display the quantity of such gaseous and liquid material. In some embodiments, the connector is adapted to modify or adjust the vacuum pressure provided by the central vacuum and/or the flow rate of the material being picked up.

One centralized evacuation system of a type suitable for use in the system of the present invention is described in U.S. Pat. No. 5,264,026, the disclosures of which patent are incorporated herein by reference. The patent discloses a centralized system for removing the plume resulting from surgical procedures, wherein the plume is drawn away from the surgical field by a vacuum. The disclosed system is suitable for vacuuming or suctioning both liquids and gas and includes a central suction device that includes a centrifugal separator and a vacuum producer. The central system is "central" because it is located in a mechanical room which is removed from or remote with respect to one or more operating rooms served by the vacuum system. Such systems include a suitable network of conduits or piping, and typically include wall inlets, ports or wall-mounted boxes with openings or ports for connecting a flexible conduit to an end effector. These end effectors may take various forms including that described in U.S. Pat. No. 4,921,492, the disclosure of which is incorporated herein by reference, and/or various embodiments thereof. As used herein the term "end effectors" is intended to encompass any structure adapted to provide for bringing a vacuum adjacent to a material or item to pick or suck up the material or item, and may include typical tubular wands or cautery tools carrying generally tubular devices which may be positioned adjacent to a surgical field to provide for removal of bioaerosol gases and/or liquids. The term is also intended to encompass such structures and devices adapted to be applied to picking up or handling both liquid and gaseous material and, in some instances, solid material.

DESCRIPTION

Features and advantages of the fluid and bioaerosol device and method of the present invention will become apparent and understood with reference to the above-noted drawings, this description and the descriptive material enclosed herewith, including the described embodiment of a connector or adaptor device for use in the system of the present invention.

With regard to fastening, mounting, attaching or connecting the components of the system of the present invention to form the connector or the system as a whole, unless specifically described otherwise, such are intended to encompass conventional fasteners such as screws, nut and bolt connectors, snap rings, clamps, such as hose clamps, screw clamps and the like, rivets, toggles, pins and the like. Components may also be connected or coupled by welding, friction fitting or deformation. Electrical components and connections may be made using appropriate electrical components and connection methods including conventional components and connectors, suitable display devices such as digital or analog devices, LED's or other light sources and the like, and suitable microprocessor or integrated circuit components. Measuring devices, such as flow meters, sensors, transducers and the like, whether for measuring volume, flow rate, or liquid or gaseous quantities, may be selected from such measuring devices which are suitable for use in the present invention. Unless otherwise specifically disclosed or taught, materials for making components of the present invention may be selected from appropriate materials such as metal, metallic alloys, fibers, plastics and the like, and appropriate manufacturing and/or production methods including casting, extruding, molding and machining may be used.

Figure 1:
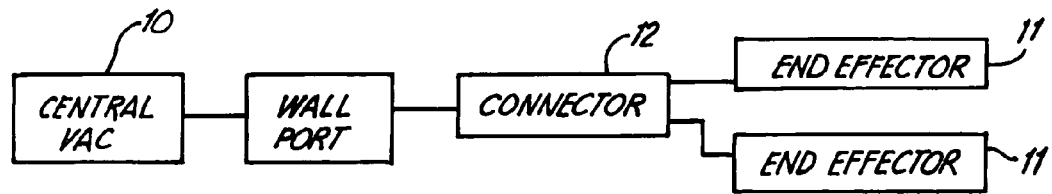
FIG. 1 depicts one embodiment of a system in accordance with the present invention.

As shown in FIG. 1, in one embodiment, the present invention comprises a central vacuum system comprising a central vacuum source 10, one or more end effectors 11 and a connector 12 interposed between the vacuum source 10 and the one or more end effectors 11, wherein the connector has at least one port for receiving gaseous and liquid fluids. In one embodiment, the system includes a suitable pipe or conduit network linking the one or more end effectors to the vacuum source.

In one embodiment, the present invention comprises a system for the handling of fluids, including bodily fluids, such as blood, and/or irrigants, such as saline solutions, within an operating room or clinical setting. Control and handling of such material includes concern for the collection and handling of infectious or disease transmission among operating room personnel. Current methods may not achieve optimum prevention of contamination of nursing and physician personnel. Bioaerosol inhalation is another recognized continuing hazard for patients and operating room personnel.

Figure 2:
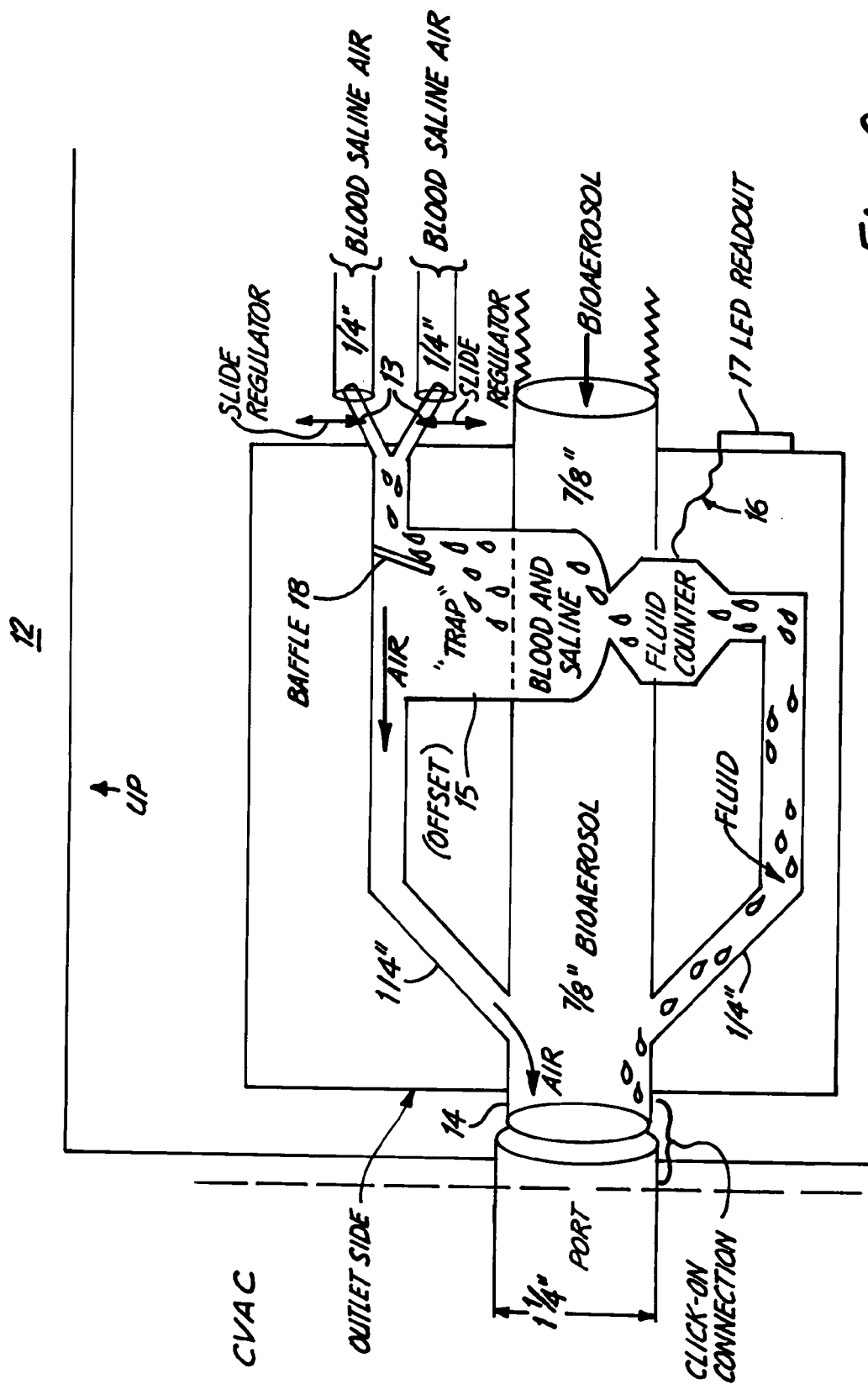
FIG. 2 depicts one embodiment of a connector in accordance with the present invention.
Figures 4, 4A:
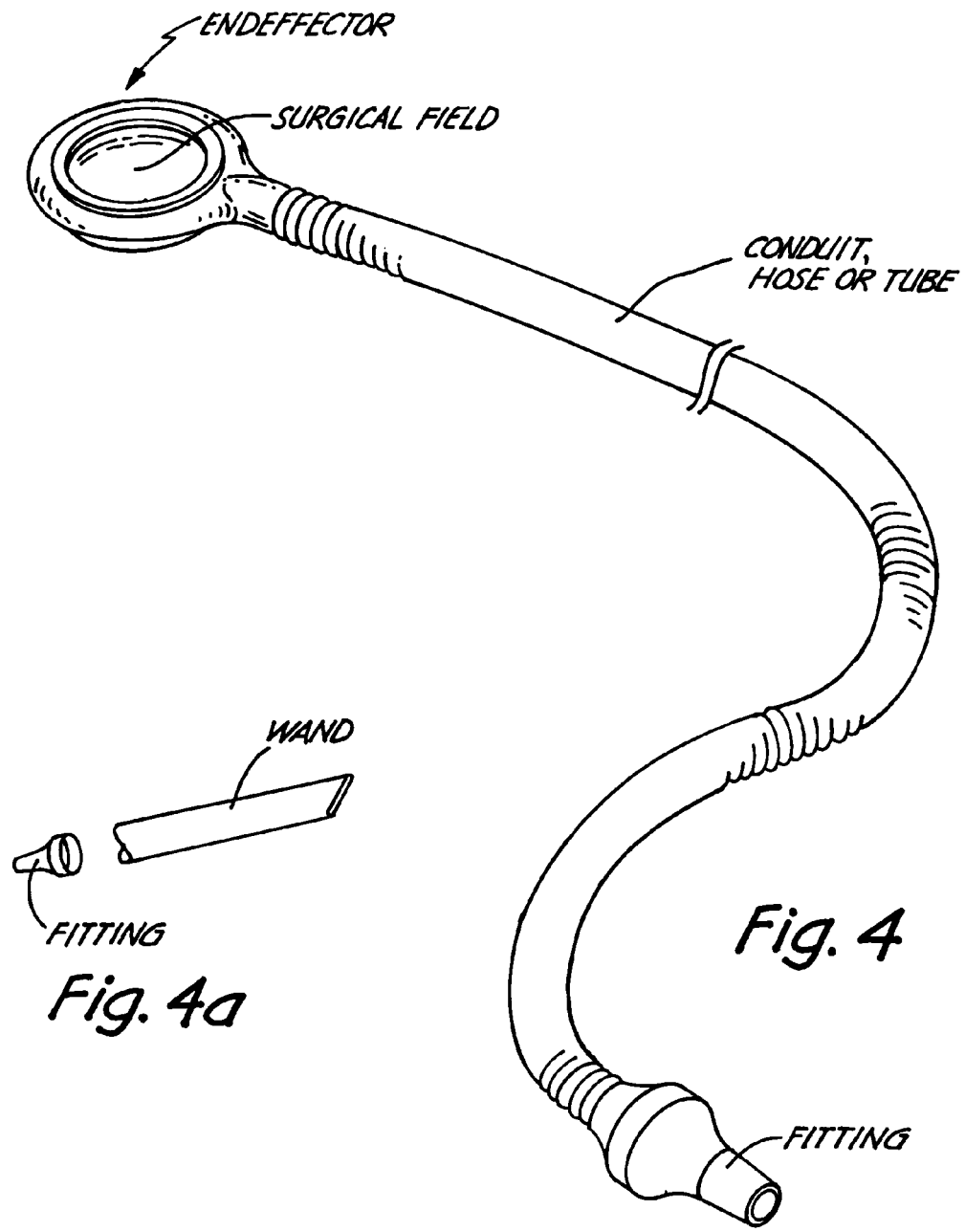
FIG. 4 depicts one embodiment of an end effector with a fluid flow depicted.
FIG. 4a depicts another end effector.

The present invention, in one embodiment, should reduce or minimize the inhalation of toxic and potentially carcinogenic inhalants and infectious liquids by providing a "no-touch" method of fluid and liquid management for use by operating room personnel. In one embodiment, as depicted in FIG. 2, the present invention comprises a central vacuum producing system suitable for collecting both liquid and gaseous material, one or more end effectors for use at a site at which liquid and gaseous material are produced, and a coupling device or connector for operably coupling one or more end effectors to the central vacuum. In this embodiment, the connector may be made of various materials, and may include a suitable liquid monitor or counter such as a flow meter.

In one embodiment, the coupling device or connector 12 of the present invention may include a volumetric measuring device for measuring the amount of bodily fluid or other liquid used during or produced during a surgical procedure. In one embodiment, the connector of the present invention may comprise suitable liquid and air media and may provide for the separation of liquid from gaseous material, yet involve a single suction source suitable for moving or collecting both liquid and gaseous material. See, for example, FIG. 1. In some embodiments, a chemical separator and separation method may be used, for example, a suitable media may be disposed in or adjacent to the port(s) of the connector.

Figure 3:
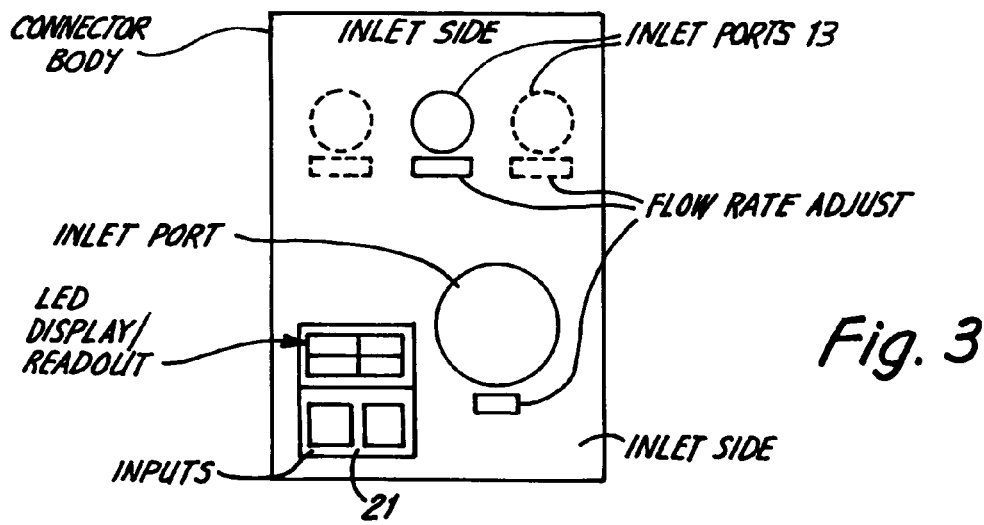
FIG. 3 is an elevational view of the connector depicted in FIG. 2.

In one embodiment, as depicted in FIGS. 1, 2 and 3, the embodiment of the connector comprises a body having an inlet side 13 and an outlet side 14. The outlet side 14 is suitably adapted to be coupled to a typical vacuum port and the inlet side 13 is adapted, as depicted in FIG. 3, to operably receive or be coupled to one or more end effectors or conduit structures leading to the end effectors. See, for example, the ports depicted in FIG. 3. Any suitable coupling or connection methods may be used including "quick-release"-type connectors, Leur-type, detent-type connectors, screw-type connectors or bayonet-type connective structures. Additionally, suitable coupling of conducts and the connector of the present invention may be accomplished by simple friction fitting.

Referring to FIGS. 1 and 2, within the body of the connector of the present invention in one embodiment there is a separating structure 15 comprising, in the depicted embodiment, a "trap" adjacent to the inlets or ports for receiving liquid as the gas/liquid combination flows across the top of the trap. The trap structure may include a suitable fluid counter, flow meter or monitor 16 for measuring the quantity of liquid passing into and/or through the trap. Both the original liquid/gas combination picked up from a surgical site and the liquid separated from the gas/liquid material are moved by the vacuum generated by the central vacuum system and are pulled into the wall port of the central vacuum system. A pump or other means may be used to move the gas and/or liquid material as well. Every conduit portion or gas and liquid flow path in the connector, or a selected conduit portion or flow path, may have a separate liquid/gas separator structure or feature, or they may be one common separator structure.

In one embodiment, the connector structure of the present invention includes more than one inlet 13, whereby more than one end effector may be coupled to the central vacuum system. Flow rates or vacuum pressures with respect to each of the inlets may be controlled separately to provide for different degrees of suction. For example, in some wand-type end effectors, a lesser degree of suction may be desired, and for certain end effectors, for example, of the "Plume-Away"-type, a greater suction may be desirable to induce a greater flow or to cover a larger area.

In some embodiments, the present invention includes an LED readout 17 for displaying the amount of liquid collected.

In other embodiments of the present invention, the liquid measuring capability may be incorporated in the main-line vacuum portion, i.e., in the wall of the operating room between the connector of the present invention and the wall port, adjacent to the wall port, or in the central mechanical room.

In some embodiments, the "trap" may include a deflector or other suitable device, e.g., a baffle 18, filter, etc., for optimizing the separation of liquid and gaseous material.

Figure 5:
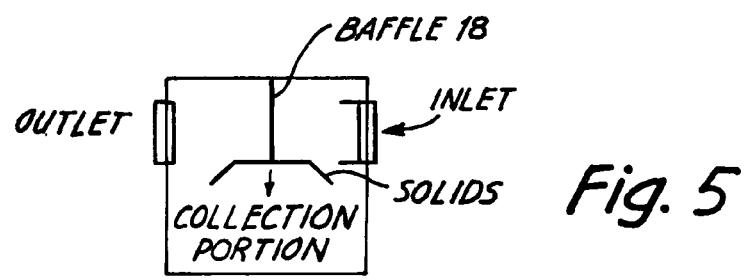
FIG. 5 depicts an adaptor for coupling to the connector for adapting the present invention to pick up solid material.

In one embodiment, the present invention may be adapted to provide several suction or vacuum related functions: removal of smoke and gaseous byproducts, general cleaning-type functions such as floor and equipment vacuuming, and liquid removal and measurement. These functions may be accomplished by providing a connector structure which connects a single central vacuum system of the type disclosed in U.S. Pat. No. 5,264,026 to various end effectors or working tools for providing various gas, liquid and/or solid management or pickup using a vacuum pressure, and an adaptor box, depicted in FIG. 5, a canister-like structure for collecting and measuring solids, and/or fluid or liquids.

In terms of method or use, in one embodiment, at the end of a surgical case or procedure, the system of the present invention may be used to clean the floor around the operating room table. Typically, such procedures result in material scattered around the floor which may include plastic wrappers or portions thereof, pieces of suture, needles, sponges, etc., as well as liquid material which needs to be picked up and decontaminated. Thus, in one embodiment, the present invention involves a suitable wall mounted vacuum port connected to a central vacuum source, the connector of the present invention, an additional adaptor, or filter, box for collection or separation of solid material and, a suitable conduit connected to the adaptor box. The box may include a suitable baffle 18 structure and/or filters to help ensure that solids collect in the collection portion of the box. In one embodiment, the adaptor box is adapted to precipitate solid material from a flow of liquid fluid, i.e., solids entrained in liquid/air flowing into the adaptor box is precipitated or dropped from the flow, and the flow enters the adaptor of the present invention and liquid is separated from the gas and quantities of liquid are assessed, after which time the flow continues into the conduit leading to the central vacuuming system. In one embodiment, the adaptor box may be reusable in that it can be emptied wherein debris collected may be disposed of conventionally. In one embodiment, the connector and/or the solids receiving adaptor or filter box may be disposable, i.e., a single use type arrangement or they may be completely reusable or reposeable in that they may last for a couple of years and then need to be replaced.

Figure 6:
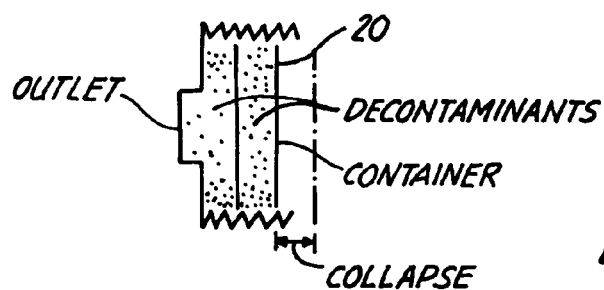
FIG. 6 depicts a decontamination container in accordance with the present invention.

Referring to FIG. 6, in the instance of reusable and reposeable type connectors and/or filter boxes, the connector and/or filter box structures may be decontaminated before a subsequent use by providing a decontamination unit 20 which comprises a suitable container structure adapted to be coupled to the connector and/or the filter box. For example, the decontamination unit may take the form of a collapsible plastic container which contains a pre-measured amount of a decontaminating, disinfecting, sterilizing or cleaning solution. In one embodiment, the decontamination unit is adapted to be attached to the filter box or to the connector, and the contents are then withdrawn upon actuation of the vacuum source. The container collapses and may be disposed. In some embodiments, the decontamination unit may include a decontaminate flow regulating mechanism or structure, and/or decontaminates may be loaded or contained in separate compartments whereby they may be dispensed together, selectively or sequentially.

As shown in FIG. 3, in one embodiment, the connector unit of the present invention may include an input feature such as a key pad counter 21, touch screen or the like whereby the quantity of liquid vacuumed up is measured and/or displayed, and wherein a known quantity of liquid, e.g., saline, anesthesia materials, etc., may be input into the device. In this embodiment, a calculation feature, e.g., a microprocessor, calculator or the like, is provided whereby the quantity of input liquid may be subtracted from the total displayed volume to calculate, for example, blood loss or saline use during a surgical procedure. Other calculations may be performed as well, such as calculation of flow rates.

The system and method of the present invention may be used in situations or applications other than the medical field. For example, in certain industries and manufacturing processes, washes or flows of liquid, mists or flows of fluids, are used for cooling or lubricating while a particular procedure is carried out. In these situations, it may be desirable to contain, control or manage the flow of cooling or lubricating material, and/or gases released during such processes, and to measure the quantity of liquid being used and/or consumed by the process. A system of the type of the present invention may be used for this, and may include, for example, a central vacuum source, a number of end effectors located a number of work stations, and one or more connectors adjacent to the workstations for removably receiving or coupling to the end effectors. Such a system may further include a suitable network of pipes or conduits, and a flow or vacuum regulating feature associated with each connector to adjust the vacuum power or pressure at the working portion of the end effectors.

In one embodiment, the present invention comprises a system for managing fluid comprising: a vacuum source, an end effector spaced from the vacuum source, and a connector interposed between the vacuum source and end effector, the connector having at least one port for receiving both gaseous and liquid fluids. More than one end effector is coupled to the connector. The connector is adapted to separate liquid and gas. The connector is adapted to regulate a vacuum applied by the end effector. The connector comprises a display, and may be provided with a display input.

In one embodiment, the present invention relates to a vacuum system for picking up fluids in an operating room, the system comprising: means for producing a vacuum and means for separating liquid and gas, both the means for producing a vacuum and means for separating liquid and gas remote from the operating room, means for applying the vacuum to a selected location in the operating room, means for defining a flow path operably coupling the means for producing a vacuum and the means for applying a vacuum, and means for operably coupling the means for applying a vacuum to the flow path. The means for operably coupling is adapted to separate liquid and gas. The means for operably coupling is adapted to regulate the vacuum applied by the end effector. The means for operably coupling comprises means for measuring a quantity of separated liquid, means for displaying the quantity, means for inputting liquid information, means for calculating a difference between the quantity of separated liquid and the liquid information, and means for displaying the quantity and the difference.

In one embodiment, the present invention comprises a vacuum system for picking up fluids and solids present in an operating room, the system comprising: a vacuum source comprising a vacuum producer and a centrifugal separator, at least one end effector, a flow path defined by conduit operably coupling the vacuum source and end effector, the flow path comprising a wall port, and a connector generally between the vacuum source and end effector and removably coupled to the wall port, wherein the connector is adapted to separate liquid and gas. The connector further comprises a measuring device for measuring the amount of liquid picked up and a display device for displaying the amount of liquid picked up. The connector is adapted to separate liquids, gas and solids. The connector further comprises an input for inputting liquid information.

In one embodiment, the present invention relates to a central vacuum system for picking up fluids present at one or more locations at which surgical procedures are performed, the system comprising: a vacuum source comprising a vacuum producer and a centrifugal separator, the vacuum source remote from the one or more locations; a first end effector of one type and a second end effector of another type; a flow path defined by conduit operably coupling the vacuum source and end effectors, the flow path comprising at least one wall port at each of the one or more locations; and a connector generally between the vacuum source and end effector and removably coupled to the wall port, the connector adapted to removably receive the first and second end effectors and to separate liquid and gas and comprising a measuring device for measuring the amount of liquid picked up and a display device for displaying the amount of liquid picked up. The invention may further comprise an adaptor for adapting the connector to separate liquids, gas and solids. The connector further comprises an input for inputting liquid information.

In one embodiment, the present invention central vacuum system for picking up material present at one or more locations at which surgical procedures are performed, the system comprising: a vacuum source comprising a vacuum producer and a centrifugal separator, the vacuum source remote from the one or more locations; a first end effector of one type and a second end effector of another type; a flow path defined by conduit operably coupling the vacuum source and end effectors, the flow path comprising at least one wall port at each of the one or more locations; and a connector generally between the vacuum source and end effectors and removably coupled to the wall port, the connector adapted to removably receive the first and second end effectors, to regulate the vacuum at the first and second end effectors, and to separate liquid and gas, and further comprising a measuring device for measuring the amount of liquid picked up, an input for inputting liquid information, a calculator for calculating a difference between the amount of liquid picked up and the input liquid information, and a display for displaying the amount of liquid picked up and the difference. The connector may be adapted to separate liquids, gas and solids.

The present invention may be embodied in other specific forms without departing from the essential spirit or attributes thereof. It is desired that described embodiments be considered in all respects as illustrative, not restrictive.

What is claimed is:

1. A vacuum connector adapted to be operably coupled to a vacuum source, the vacuum connector comprising:
   one or more inlets, at least one of which is adapted to be operably coupled with an end effector;
   an outlet adapted to be operably coupled with the vacuum source;
   one or more separation chambers in communication with one or more of the inlets;
   an air pathway from the separation chamber to the outlet;
   a fluid pathway from the separation chamber to the outlet, the fluid pathway being separate from the air pathway; and
   a removable decontamination unit adapted to be coupled to an inlet of the connector;
   wherein the decontamination unit comprises a collapsible container containing a pre-measured amount of decontaminating solution; and
   wherein the collapsible container is configured such that upon actuation of the vacuum source, the decontaminating solution flows from the collapsible container to the separation chamber and the collapsible container collapses.

2. The vacuum connector of claim 1, wherein the separation chamber includes a baffle in cooperation with the inlet for optimizing the separation of liquid and gaseous material.

3. A vacuum system comprising:
   a vacuum source;
   a connector comprising an inlet, an outlet coupled directly with the vacuum source, wherein the vacuum source is positioned downstream from the outlet, a separation chamber in communication with the inlet, an air pathway in communication with the separation chamber and the outlet, and a fluid pathway separate from the air pathway and in communication with the separation chamber;
   an end effector in communication with the inlet; and
   a removable decontamination unit adapted to be coupled to the connector;
   wherein the decontamination unit comprises a collapsible container containing a pre-measured amount of decontaminating solution; and
   wherein the collapsible container is configured such that upon actuation of the vacuum source, the decontaminating solution flows from the collapsible container to the separation chamber and the collapsible container collapses.

4. A vacuum system comprising:
   a vacuum source;
   a connector comprising an inlet, an outlet operably coupled directly with the vacuum source, wherein the vacuum source is positioned downstream from the outlet, a separation chamber in communication with the inlet, an air pathway from the separation chamber to the outlet, and a fluid pathway separate from the air pathway, from the separation chamber to the outlet;
   an end effector in communication with the inlet; and
   a removable decontamination unit adapted to be coupled to the connector, wherein the decontamination unit comprises a collapsible container containing a pre-measured amount of decontaminating solution, wherein the collapsible container is configured such that upon actuation of the vacuum source, the decontaminating solution flows from the collapsible container to the separation chamber and the collapsible container collapses.

5. The system of claim 4, further comprising a flowmeter coupled to the fluid pathway, and a microprocessor in communication with the flowmeter and capable of calculating flow rates and total volume.

6. The system of claim 5, further comprising an input device in communication with the microprocessor.

7. The system of claim 6, wherein the input device includes a key pad.

8. The system of claim 4, wherein the connector further comprises a collection chamber in communication with the separation chamber.

9. The system of claim 4, wherein the connector further comprises a vacuum regulator in cooperation with the inlet.

10. The system of claim 4, wherein the separation chamber includes a baffle in cooperation with the inlet for optimizing the separation of liquid and gaseous material.

11. The system of claim 4, wherein the separation chamber includes a filter in cooperation with the inlet for optimizing the separation of solid materials.

* * * * *